(12) United States Patent
Pardo

(10) Patent No.: US 9,050,282 B2
(45) Date of Patent: Jun. 9, 2015

(54) METHOD OF PROVIDING PROTECTIVE IMMUNITY AGAINST HETEROLOGOUS LEPTOSPIRA STRAINS

(71) Applicant: Maria Camila Pardo, Athens, GA (US)

(72) Inventor: Maria Camila Pardo, Athens, GA (US)

(73) Assignee: MERIAL, INC., Duluth, GA (US)

( * ) Notice: Subject to any disclaimer, the term of this patent is extended or adjusted under 35 U.S.C. 154(b) by 0 days.

(21) Appl. No.: 13/939,300

(22) Filed: Jul. 11, 2013

(65) Prior Publication Data

US 2014/0023678 A1 Jan. 23, 2014

Related U.S. Application Data

(60) Provisional application No. 61/672,386, filed on Jul. 17, 2012.

(51) Int. Cl.
*A61K 49/00* (2006.01)
*A61K 39/23* (2006.01)
*A61K 39/00* (2006.01)
*A61K 39/02* (2006.01)

(52) U.S. Cl.
CPC .............. *A61K 39/0225* (2013.01); *A61K 39/00* (2013.01); *A61K 2039/521* (2013.01); *A61K 2039/552* (2013.01); *A61K 2039/70* (2013.01)

(58) Field of Classification Search
CPC ... A61K 39/12; A61K 39/0225; A61K 39/29; A61K 39/235; A61K 39/295; A61K 39/155; A61K 39/175; A61K 39/205; C07K 14/20; G01N 2333/20
USPC .................. 424/9.1, 9.2, 184.1, 204.1, 213.1, 424/221.1, 224.1, 233.1
See application file for complete search history.

(56) References Cited

U.S. PATENT DOCUMENTS

2008/0181916 A1* 7/2008 Callister et al. ............ 424/234.1

OTHER PUBLICATIONS

Rinehart CL et al. Protection for *Lepto borgpetersenii* serovar handjo using Express® FP. 2012.
Pena-Moctezuma, A. et al. Genetic differences among the LPS biosynthetic loci of serovars of *Leptospira interrogans* and *Leptospira borgpetersenii*. FEMS Immunology and Medical Microbiology 31 (2007) 73-81).
Fernandez et al. Efficacy of Leptospiral vaccinge (vax-SPIRAL®) against challenge with strains isolated from leptospirosis epidemic in Nicaragaua using the hamster biomodel. Vet. World, 2012, vol. 5(1): 5-12.
WHO. "Leptospirosis Fact Sheet"(WHO, Regional Office for South-East Asia, 2009).
NOBIVAC® Lepto 1 Safety Data Sheet. MSD Animal Health. Sep. 2011.
Lepto 2 Way and Lepto 3 Way product information sheet. Virbac. 2012.
Nascimento, A.L.T.O. et al. Comparative genomics of two Leptospira interrogans serovars reveals novel insights into physiology and pathogeneses. Journal of Bacteriology, 186(7):2164-2172, 2004.
Nascimento, A.L.T.O. et al. Genome features of Leptospira interrogans serovar Copenhageni. Braz J Med Biol Res. Apr. 2004; 37(2).
RECOMBITEK® 4 LEPTO (Merial Limited) News Release. Aug. 2, 2010.

* cited by examiner

*Primary Examiner* — Rodney P Swartz
(74) *Attorney, Agent, or Firm* — Judy Jarecki-Black; Chad Kitchen Merial, Inc.

(57) ABSTRACT

The present invention provides compositions and methods for eliciting protective immunity in animals against *Leptospira interrogans* (LI) serovar *copenhageni*. The invention is based, in part, on the unexpected cross-protection against heterologous LI serovar, which resulted when canines were administered an effective amount of RECOMBITEK® 4 Lepto, then subsequently challenged with virulent *L. copenhageni* (Fiocruz L1-130).

5 Claims, 1 Drawing Sheet

METHOD OF PROVIDING PROTECTIVE IMMUNITY AGAINST HETEROLOGOUS LEPTOSPIRA STRAINS

INCORPORATION BY REFERENCE

Figure 1:
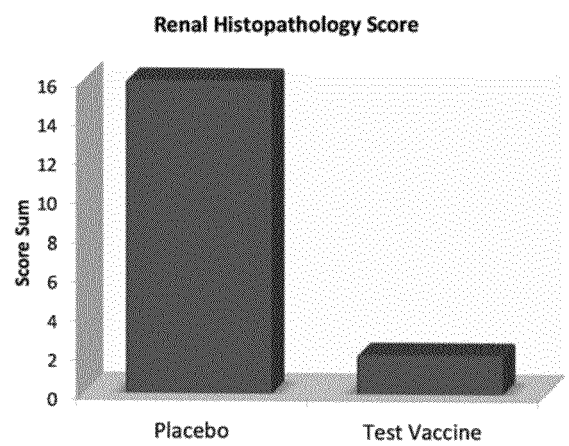
Figure 2:
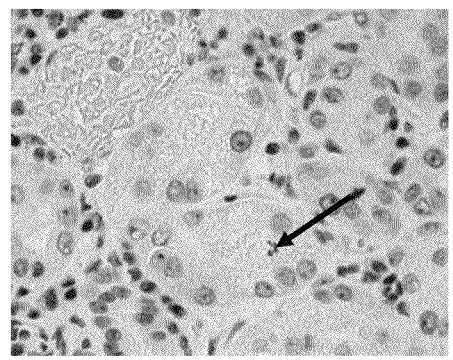

This application claims priority to provisional application U.S. Ser. No. 61/672,386, filed on Jul. 17, 2012, and incorporated by reference herein in its entirety.

FIELD OF THE INVENTION

The present invention relates generally to immunogenic *leptospira* compositions, which are capable of eliciting cross-protective immune responses in animals, particularly canine animals. The invention further relates to methods of providing animals, especially canine animals, with cross-protective immune responses against *leptospira*.

BACKGROUND OF THE INVENTION

Leptospirosis is an important world-wide zoonosis, caused by spirochetes from the *Leptospira* genus. It is an occupational hazard for many people who work outdoors or with animals, including farmers, veterinarians, meat workers, dairy farmers, and military personnel. It is a recreational hazard for campers, or those who participate in outdoor sports in contaminated areas, and has been associated with swimming, wading, and whitewater rafting. Outbreaks of leptospirosis are usually caused by exposure to water contaminated with the urine of infected animals. Many different kinds of animals carry the bacterium; they may become sick but sometimes have no symptoms. *Leptospira* organisms have been found in cattle, pigs, horses, dogs, rodents, and wild animals, including marine mammals. Humans become infected through contact with water, food, or soil containing urine from these infected animals. This may happen by swallowing contaminated food or water or through skin contact, especially with mucosal surfaces such as the eyes or nose, or with broken skin.

The most common serovars reported in the United States are *L. icterohaemorrhagiae*, *L. canicola*, *L. grippotyphosa* and *L. bratislava*. Another serovar of interest reported in Latin America, is *L. interrogans* serovar *copenhageni*. This serovar belongs to the *Icterohaemorrhagiae* serogroup, and has similarities in the DNA sequence for known colonization virulence factors, and appears to be responsible for most canine leptospirosis in New Zealand.

Review of the Literature

"Leptospirosis Fact Sheet" (WHO, Regional Office for South-East Asia, 2009) indicates, in part, that animals and humans can be immunized, but that protection is largely serovar-specific. Lack of cross-protection is not surprising, particularly in view of the significant genetic/genomic differences, for example, among the gene organization in the lipopolysaccharide biosynthetic (rfb) locus (Pena-Moctezuma, A. et al., 2001 FEMS Immunology and Medical Microbiology 31 (2001) 73-81).

Nascimento, A. L. T. O. et al. Comparative genomics of two *Leptospira interrogans* serovars reveals novel insights into physiology and pathogenesis. Journal of Bacteriology, 186(7):2164-2172, 2004.

Nascimento, A. L. T. O. et al. Genome features of *Leptospira interrogans* serovar *copenhageni*. Braz J Med Biol Res. 2004 Apr; 37(2).

Recombitek Lepto 4 (Merial Limited)—contains *Leptospira icterohaemorrhagiae* (LI) was obtained from National Animal Disease Center (NADC), Ames, Iowa, on 28 Feb. 1968 by Dow Chemical, Zionsville, Ind. The vaccine further contains *Leptospira grippotyphosa*, *L. canicola*, and *L. pomona* serovars.

Novibac (Merck Animal Health)—contains *L. interrogans* serogroup *canicola* serovar *portlandvere* (strain Ca-12-000); *L. interrogans* serogroup *icterohaemorrhagiae* serovar *copenhageni* (strain Ic-02-001); *L. interrogans* serogroup *australis* serovar *bratislava* (strain As-05-073); and *L. kirschneri* serogroup *grippotyphosa* serovar *dadas* (strain Gr-01-005). Company-provided data indicates, unsurprisingly, the *copenhageni*-containing vaccine elicits in canine an immune response against serovar *copenhageni*. This product label claim is also consistent with what is well-known in the *Leptospira* arts, namely, that little if any evidence for "cross-protection", which is herein defined as providing protection against a heterologous *Leptospira* serovar by administering an effective amount of a different serovar (e.g. protecting against *copenhageni* by administering a homologous effective amount of a non-*copenhageni* LI *icterohaemorrhagiae* serogroup Leptospire.

Thus, as an alternative to vaccinating animals using all lepto serovars against which immunological protection is desired, it would be useful to provide new methods of eliciting cross-protective immune responses against different lepto serovars. Until the instant disclosure, methods for providing protection against LI *copenhageni* using non-*copenhageni* serovars were not known.

SUMMARY OF THE INVENTION

An object of this invention is to provide methods for providing protective immunity against a first *Leptospira* serovar comprising the step of administering a second *Leptospira* serovar(s), which is from a different serogroup and/or serovar, with respect to the first *Leptospira* serovar. In the cases where the second *Leptospira* serovar(s) is a combination of *Leptospira* serovars (e.g. a combination/multi-valent vaccine), the second *Leptospira* serovar(s) must not contain or comprise a *Leptospira* serovar of the same serovar as the first *Leptospira* serovar, for which protective immunity is being sought.

In an embodiment, the methods provide protective immunity against *Leptospira Icterohaemorrhagiae* (LI) serovar *copenhageni*, and comprise the step of administering an effective amount of a non-*copenhageni* LI serovar to an animal in need thereof.

In a particular embodiment, the non-*copenhageni* LI serovar is from the $24^{th}$ passage of LI obtained from National Animal Disease Center (NADC), Ames, Iowa, on 28 Feb. 1968 by Dow Chemical, Zionsville, Ind.

In another embodiment, the methods provide protective immunity against LI serovar *copenhageni* by administering a combination/multivalent *Leptospira* vaccine. In a particular embodiment, the vaccine is Merial's RECOMBITEK® 4 Lepto, as made in the United States as of Jun. 25, 2012. In an embodiment, the 4 Lepto comprises *Leptospira canicola, Leptospira grippotyphosa, Leptospira icterohaemorrhagiae, Leptospira pomona* (all chemically inactivated) and has label claims (as of Jun. 25, 2012) according to the following: "provides protection against *Leptospira grippotyphosa* for 15 months and prevents shedding of *Leptospira spirochetes* in the urine. Specifically the vaccine is labeled to prevent Leptospirosis and Leptospiruria caused by *L. icterohaemorrhagiae, L. canicola, L. grippotyphosa*. It also aids in the prevention of Leptospirosis and Leptospiruria caused by *L. Pomona.*"

In a particular embodiment, and unexpected/surprising to the skilled worker in possession of the current state-of-the-art knowledge in the field of leptospirosis, the invention provides for administration of Merial's RECOMBITEK® 4 Lepto to canines to elicit protective immunity against a first LI serovar, which is not contained within the 4-way vaccine, and which is LI serovar *copenhageni*.

These and other embodiments are disclosed or are obvious from and encompassed by, the following Detailed Description.

BRIEF DESCRIPTION OF DRAWINGS

A full and enabling disclosure of the present invention, including the best mode thereof, to one of ordinary skill in the art, is set forth more particularly in the remainder of the specification, including reference to the accompanying figures, wherein:

FIG. 1 provides a graph of renal histopathology scores by group;

FIG. 2 is an image of kidney immunohistochemistry (40×) from a control dog with acute leptospirosis. Arrow indicates the presence of leptospira spirochete in the renal tubules.

DETAILED DESCRIPTION OF THE INVENTION

The present invention encompasses methods for prevention of infection due to Leptospires of a particular serovar by administering Leptospires of a different serovar.

In an embodiment, the invention provides methods of eliciting in an animal a protective immune response against *Leptospira interrogans* serovar *copenhageni* comprising the step of administering to the animal an effective amount of a non-*copenhageni Leptospira* serovar.

In an embodiment, the non-*copenhageni Leptospira* serovar is delivered as part of a multivalent/combination vaccine. In a particular embodiment, the non-*copenhageni* Lepto serovar is LI *icterohaemorrhagiae.*

In another embodiment, the vaccine comprises *Leptospira interrogans* (LI) serovar *icterohaemorrhagiae*. In still another embodiment, the vaccine comprises LI *icterohaemorrhagiae*, LI *canicola*, LI *grippotyphosa*, and LI *pomona.*

In a particular embodiment, the vaccine is Merial's RECOMBITEK® 4 Lepto, as manufactured in June 2012.

Descriptions/Definitions

The "LI serovar Ictero" seed from RECOMBITEK® 4 Lepto is identified herein as ictero, which was obtained from National Animal Disease Center (NADC), Ames, Iowa, on 28 Feb. 1968 by Dow Chemical, Zionsville, Ind. On 17 Dec. 1971, the seed was transferred to Pitman-Moore, Inc., License No. 264, Washington Crossing, N.J. A master seed was prepared by Dow at the 20th passage. Pitman-Moore, Inc., produced a master seed after three passages in artificial medium on 21 Jan. 1975 as "LI 1508 P23." A master seed was also qualified by Pitman-Moore, Inc., identified as "LI SC1518, P24 MS, Aug. 18, 1976." Rhone Merieux, Inc. (now known as Merial, Inc.), License No. 298, received a culture from Pitman-Moore, Inc., on 30 Jun. 1988 identified as "LI SC1518 P24 MS Aug. 18, 1976".

The "LI serovar *copenhageni*" challenge strain was of different origin and serogroup/serovar, when compared to the vaccination serovars (isolated from a human in Brazil, and designated: Fiocruz L1-130).

By "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a polypeptide, an epitope, a hapten, or any combination thereof. Alternately, the immunogen or antigen may comprise a toxin or antitoxin.

The terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

The term "immunogenic or antigenic polypeptide" as used herein includes polypeptides that are immunologically active in the sense that once administered to the host, it is able to evoke an immune response of the humoral and/or cellular type directed against the protein. Preferably the protein fragment is such that it has substantially the same immunological activity as the total protein. Thus, a protein fragment according to the invention comprises or consists essentially of or consists of at least one epitope or antigenic determinant. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above. Such fragments can be identified using any number of epitope mapping techniques, well known in the art. See, e.g., Epitope Mapping Protocols in Methods in Molecular Biology, Vol. 66 (Glenn E. Morris, Ed., 1996). For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., 1984; Geysen et al., 1986. Similarly, conformational epitopes are readily identified by determining spatial conformation of amino acids such as by, e.g., x-ray crystallography and 2-dimensional nuclear magnetic resonance. See, e.g., Epitope Mapping Protocols, supra. Methods especially applicable to the proteins of T. parva are fully described in PCT/US2004/022605 incorporated herein by reference in its entirety.

As discussed herein, the invention encompasses active fragments and variants of the antigenic polypeptide. Thus, the term "immunogenic or antigenic polypeptide" further contemplates deletions, additions and substitutions to the sequence, so long as the polypeptide functions to produce an immunological response as defined herein. The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cystine, serine, threonine, tyrosine. Phenylalanine, tryptophan, and tyrosine are sometimes classified as aromatic amino acids. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic acid for aspartic acid, or glutamine for asparagine, and the like; or a similar conservative replacement of an amino acid with a structurally related amino acid that will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide. All of the polypeptides produced by these modifications are included herein. The term "conservative variation" also includes the use of a substituted amino acid in place of an unsubstituted parent amino acid provided that antibodies raised to the substituted polypeptide also immunoreact with the unsubstituted polypeptide.

The term "epitope" refers to the site on an antigen or hapten to which specific B cells and/or T cells respond. The term is also used interchangeably with "antigenic determinant" or "antigenic determinant site". Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms and/or clinical disease signs normally displayed by an infected host, a quicker recovery time and/or a lowered viral titer in the infected host.

By "animal" is intended mammals, birds, and the like. Animal or host as used herein includes mammals and human. The animal may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), ovine (e.g., sheep), bovine (e.g., cattle), porcine (e.g., pig), avian (e.g., chicken, duck, goose, turkey, quail, pheasant, parrot, finches, hawk, crow, ostrich, emu and cassowary), primate (e.g., prosimian, tarsier, monkey, gibbon, ape), ferrets, seals, and fish. The term "animal" also includes an individual animal in all stages of development, including newborn, embryonic and fetal stages.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicate otherwise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

The invention will now be further described by way of the following non-limiting examples.

EXAMPLES

Example 1

Cross-Protection of Recombitek® 4 Lepto gainst a *Leptospira Interrogans* Serovar *Copenhageni* Challenge in Dogs Objective. To evaluate cross protection of RECOMBITEK® 4 Lepto against a *Leptospira interrogans* serovar *copenhageni* challenge in dogs.

Materials and Methods. Twenty-four (24) purpose-bred beagles, approximately 2 months old, were randomly divided into two groups of 12 dogs each. One group was administered Recombitek® 4 Lepto and the other group a placebo vaccine (PBS). All dogs received 2 subcutaneous doses (1 ml) of the vaccine at a 21-day interval. Dogs from both groups were commingled during the entire study. Approximately 4 weeks after the second vaccination all dogs were sedated and administered *L. copenhageni* challenge at 4.7 x $10^8$ lepto spirochetes/ml, 10 mls intraperitoneally and 0.2 ml instilled topically per eye in the conjunctival sac. Following challenge, blood was collected periodically for liver profile and *leptospira* re-isolation. Sera samples were tested for serovar specific antibody by microaglutination test at regular intervals. Urine was collected periodically for re-isolation of *leptospira*. Dogs were subject to necropsy at the end of the study and kidneys were harvested for histopathology and *leptospira* re-isolation.

TABLE 1

Study Design

| GROUP | DOGS PER GROUP | VACCINE GROUP | ROUTE/ DOSE | FREQUENCY | CHALLENGE* (29 Days post V2) |
|---|---|---|---|---|---|
| A | 12 | Recombitek ® 4 Lepto | SC/1 ml | Twice, 21 days apart | Conjunctival 0.2 ml/ Intraperitoneal 10 ml |
| B | 12 | Placebo (PBS) | SC/1 ml | Twice, 21 days apart | |

*Challenge dose: 4.7 x $10^8$ organisms per ml, approximately $10^{9.73}$ organisms per dog.

Results. Dogs with mortality following *L. copenhageni* challenge prior to planned necropsies were classified as having acute leptospirosis if one of the kidneys was positive for leptospirosis by immunohistochemistry and/or the histopathological lesions were indicative of acute leptospirosis. Dogs that underwent necropsy at the end of the study were classified as having disease due to *L. copenhageni* if it had one or more positive urine samples and a renal histopathology score greater than or equal to 1 for either kidney.

TABLE 2

Incidence of disease, leptospiuria and leptospiremia

| Group Name | (−) | (+) |
|---|---|---|
| *Incidence of disease due to L. copenhageni challenge* | | |
| Placebo (PBS) | 1 | 10 |
| Test Vaccine (Recombitek ® 4 Lepto) | 9 | 2 |
| p-value of Fisher's exact Test | | P ≤ 0.01 |
| *Leptospiuria - presence of leptospira in the urine* | | |
| Placebo (PBS) | 2 | 7 |
| Test Vaccine (Recombitek ® 4 Lepto) | 8 | 1 |
| P-value of Fisher's exact Test | | P ≤ 0.05 |
| *Leptospiremia - presence of leptospira in the blood* | | |
| Placebo (PBS) | 1 | 10 |
| Test Vaccine (Recombitek ® 4 Lepto) | 9 | 1 |
| p-value of Fisher's exact Test | | P ≤ 0.01 |

TABLE 3

Clinical signs - incidence and duration post-challenge

| Clinical Signs | Group | Total number of dogs | Mean duration (days) |
|---|---|---|---|
| Depression | Placebo (PBS) | 3/11 | 2.3 |
| | Recombitek ® 4 Lepto | 0/11 | NA |
| Dehydration | Placebo (PBS) | 3/11 | 1 |
| | Recombitek ® 4 Lepto | 1/11 | 1 |
| Icterus | Placebo (PBS) | 3/11 | 3 |
| | Recombitek ® 4 Lepto | 0/11 | NA |
| Conjunctivitis | Placebo (PBS) | 9/11 | 15.4 |
| | Recombitek ® 4 Lepto | 5/11 | 7.8 |

Conclusions. This is the first time we report cross protection of Recombitek® 4 Lepto against a *L. copenhageni* challenge in dogs. These data are both surprising and unexpected in view of the overwhelming majority of literature references, which collectively teach vaccination with a particular *leptospira* species does not provide protective immune responses against heterologous *leptospira* species (see especially the "Leptospirosis Fact Sheet" (WHO, 2009) and Pena-Moctezuma, A. et al., 2001). The incidence of leptospirosis, and *leptospira* re-isolation from blood and urine was significantly higher in the placebo group in comparison to the Recombitek® Lepto 4 group. Dogs in the placebo group had higher incidence of depression, dehydration, icterus and conjunctivitis. All dogs in the placebo group had a renal histopathology score of 1 or greater. Mean ALP, ALT, BUN and creatinine values on specific days were higher in the placebo group in comparison to the Recombitek® Lepto 4 group.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method of providing a canine in need of protective immunity against *Leptospira interrogans* serovar *copenhageni* said immunity against *Leptospira interrogans* serovar *copenhageni* comprising administering to the canine a vaccine consisting essentially of an effective amount of a *Leptospira icterohaemorrhagiae* (LI) serovar, a *Leptospira grippotyphosa* serovar, a *L. canicola* serovar, and a *L. pomona* serovar.

2. The method of claim 1 wherein the *Leptospira icterohaemorrhagiae* (LI) serovar, the *Leptospira grippotyphosa*, the *L. canicola* serovar, and the *L. pomona* serovar are attenuated, such that they do not cause disease in the canine.

3. The method of claim 1 or 2 wherein the animal is administered about 1 ml of vaccine.

4. The method of claim 3 wherein the animal is administered 2 subcutaneous doses.

5. The method of claim 4 wherein the 2 doses are administered at a 21-day interval.

\* \* \* \* \*